United States Patent
Clark et al.

(10) Patent No.: US 10,864,221 B1
(45) Date of Patent: Dec. 15, 2020

(54) NEUROPROTECTIVE MIXTURE FOR MITIGATING THE HARMFUL EFFECTS OF ISCHEMIC STROKE

(71) Applicant: Tricerapro Holding, LLC, Morgantown, WV (US)

(72) Inventors: Joseph L. Clark, Cincinnati, OH (US); Todd J. Crocco, Morgantown, WV (US); Charles L. Rosen, Morgantown, WV (US); Steven Cutright, Morgantown, WV (US)

(73) Assignee: TRICERAPRO HOLDING, LLC, Morgantown, WV (US)

( * ) Notice: Subject to any disclaimer, the term of this patent is extended or adjusted under 35 U.S.C. 154(b) by 0 days.

(21) Appl. No.: 16/354,994

(22) Filed: Mar. 15, 2019

Related U.S. Application Data

(60) Provisional application No. 62/694,983, filed on Jul. 7, 2018.

(51) Int. Cl.
| | |
|---|---|
| *A61K 31/661* | (2006.01) |
| *A61P 25/00* | (2006.01) |
| *A61K 31/191* | (2006.01) |
| *A61K 31/22* | (2006.01) |

(52) U.S. Cl.
CPC .......... *A61K 31/661* (2013.01); *A61K 31/191* (2013.01); *A61K 31/22* (2013.01); *A61P 25/00* (2018.01)

(58) Field of Classification Search
CPC ............ A61K 31/4168; A61K 31/4172; A61K 47/62; A61P 25/00
See application file for complete search history.

(56) References Cited

PUBLICATIONS

Jowko et al., "Creatine and b-Hydroxy-b-Methylbutyrate (HMB) Additively Increase Lean Body Mass and Muscle Strength During a Weight-Training Program", Nutrition, 2001, vol. 17, pp. 558-566 (Year: 2001).*

Peña Cunha et al., "Both Creatine and Its Product Phosphocreatine Reduce Oxidative Stress and Afford Neuroprotection in an In Vitro Parkinson's Model", ASN Neuro, Oct.-Dec. 2014, pp. 1-16 (Year: 2014).*

Tieu et al., "D-β-Hydroxybutyrate rescues mitochondrial respiration and mitigates features of Parkinson disease", J. Clin. Invest., 2003, vol. 112, No. 6, pp. 892-902 (Year: 2003).*

"Magnesium in the Central Nervous System", University of Adelaide Press, 2011, Chapters 3, 17, and 23 (Year: 2011).*

Institute of Medicine (US) Committee on Nutrition, Trauma, and the Brain; Erdman J, Oria M, Pillsbury L, editors. Nutrition and Traumatic Brain Injury: Improving Acute and Subacute Health Outcomes in Military Personnel, 2011, Chapter 10, Creatine. https://www.ncbi.nlm.nih.gov/books/NBK209321/ (Year: 2011).*

Suzuki et al., Jpn. J. Pharmacol., 2001, vol. 87, pp. 143-150 (Year: 2001).*

* cited by examiner

*Primary Examiner* — Savitha M Rao
(74) *Attorney, Agent, or Firm* — Birch, Stewart, Kolasch & Birch, LLP

(57) ABSTRACT

A neuroprotective mixture includes Phosphocreatine (PCr), Magnesium Gluconate (MgG), and β-hydroxybutyrate (BHB). The PCR, MgG, and BHB are combined in a 2:1:2 molar ratio of PCr:MgH:BHB. The neuroprotective mixture is a useful preventative and prophylactic supplement, which also can function to extend the post-stroke treatment window.

1 Claim, 5 Drawing Sheets
(5 of 5 Drawing Sheet(s) Filed in Color)

BOXes Control            BOXes and TCP

Control Stress Gene Expression (HSP25)

BOXes Control            BOXes and TCP

Saline Control      TCP Administration

Saline Control      TCP Administration

NEUROPROTECTIVE MIXTURE FOR MITIGATING THE HARMFUL EFFECTS OF ISCHEMIC STROKE

CROSS REFERENCE TO RELATED APPLICATIONS

This application claims the benefit of U.S. Provisional Application No. 62/694,983, filed Jul. 7, 2018, the contents of which are incorporated herein by reference.

FIELD OF INVENTION

The present disclosure relates to the use of supplements to mitigate the harmful effects of ischemic stroke, hemorrhagic stroke, or any condition that includes aberrant perfusion of the brain.

BACKGROUND

Stroke causes cerebral vascular damage, which often results in permanent disability or death. The events associated with the cerebral vascular damage caused by stroke include ischemia, reperfusion injury, perfusion dysfunction, and metabolic failure. Interventions such as thrombolytic therapy with tissue plasminogen activator (tPA) have been shown to improve clinical outcome for a subgroup of ischemic stroke patients treated within four and a half (4.5) hours of symptom onset. While the window of opportunity for effective intravenous treatment is four and a half (4.5) hours, the intra-arterial therapeutic window is six (6) hours in length. Such limited time frames have challenged health care systems to reevaluate and redesign their whole approach to stroke treatment. Previous studies into the intravenous use of tPA have found a low rate of patient eligibility. Patient recruitment rates have been as low as between 1.1% and 8% of patients screened.

In the National Institute of Neurological Disorders and Stroke study of thrombolysis with tPA in 1995, there was only a 3.6% rate of patient eligibility, and this rate did not pass 5% in the subsequent ten (10) years. Consequently, other modalities of stroke care are being investigated including therapies that are applicable for the acute hemorrhagic stroke patient.

Among the other stroke treatments that are being investigated are the neuroprotective agents. At least forty (40) separate neuroprotective agents have been studied to date. These include NMDA (N-Methyl-D-Aspartate) antagonists, aptiganel, eliprodil, channel blockers, sodium channel blockers, free radical scavengers, and promoters of cell membrane repair. None of the neuroprotective trials have demonstrated clinical efficacy in the human setting despite promising results in animal models. Several explanations have been offered to address this issue.

First, the animal models have largely utilized young and otherwise healthy stock, which does not reflect the usual human condition involved in stroke.

Second, the time window for neuroprotective agent administration has been twelve (12) hours or more in several of the neuroprotective trials. Data gathered from studies pertaining to the use of intravenous and intra-arterial tPA have suggested that the therapeutic window for neuronal salvage is significantly shorter than this therapeutic window.

Third, previous neuroprotective agents have been single chemicals targeting a specific mechanism in cellular death or injury. For example, antioxidants, vasodilators, or other metabolic protectors have been attempted individually. In general, these agents have been one-dimensional in their mechanisms of action.

Thus, there remains a need for a prophylactic neuroprotective mixture that reduces the devastating effects of stroke, and in the occurrence of stroke, minimizes the damage to the brain and blood vessels.

SUMMARY

The present invention solves the foregoing problems by providing a mixture of three compounds, which together can mitigate the neuronal injury caused by ischemic stroke, hemorrhagic stroke, and aberrant cerebral perfusion states. In one of the many preferred embodiments, these compounds can include Phosphocreatine (PCr), Magnesium Gluconate (MgG) and β-hydroxybutyrate (BHB). Together these three compounds synergistically protect the brain, the blood vessels, and the blood brain barrier following stroke. For convenience purposes, the mixture of compounds may be referred to herein as "TCP."

A feature of the invention is that the mixture is not a definitive or primary therapy, but rather the mixture is a neurovascular and neuronal protective combination therapy, which preserves neuronal viability until more definitive therapeutic and/or recanalization strategies can be implemented.

An advantage of the invention is that the mixture is stable at room temperature and can be administered safely and it is well-tolerated by humans.

Another advantage of the invention is that the mixture can limit the damage to neurons caused by ischemic and hemorrhagic strokes or aberrant cerebral perfusion states.

The neuroprotective mixture of the present invention, with its multidimensional and synergistic mechanisms of action coupled with its prophylactic/preventative administration strategy, represents a significant departure from previous attempts at neuroprotection.

Individuals that sustain acute ischemic stroke, acute hemorrhagic stroke, and aberrant cerebral perfusion states will benefit from this neuroprotective supplement.

One aspect of the invention is delivery and administration of the neuroprotective mixture in an oral preparation as a preventative or prophylactic supplement. The administration can be in the form of a capsule, liquid, pill, or any other mechanism known to one skilled in the art. Dosing amounts can be based upon a standardized patient weight.

A second aspect of the invention is that it will contribute to a safe and effective neuroprotectant for the acute stroke patient. The neuroprotective mixture inhibits irreparable brain injury until reperfusion can be established.

The neuroprotective mixture is a tri-functional system that protects the brain, blood vessels, and blood brain barrier. The mixture is a novel approach to neuroprotection that favorably affects the events inherent in cellular death that occur in ischemic stroke, hemorrhagic stroke, and aberrant cerebral perfusion states. This mixture further presents a novel method of use and delivery as an oral supplement providing neuronal protection in a preventative and prophylactic manner.

BRIEF DESCRIPTION OF THE DRAWINGS

The patent or application file contains at least one color drawing. Copies of this patent or patent application publication with color drawing will be provided by the USPTO upon request and payment of the necessary fee.

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION

Figure 1:
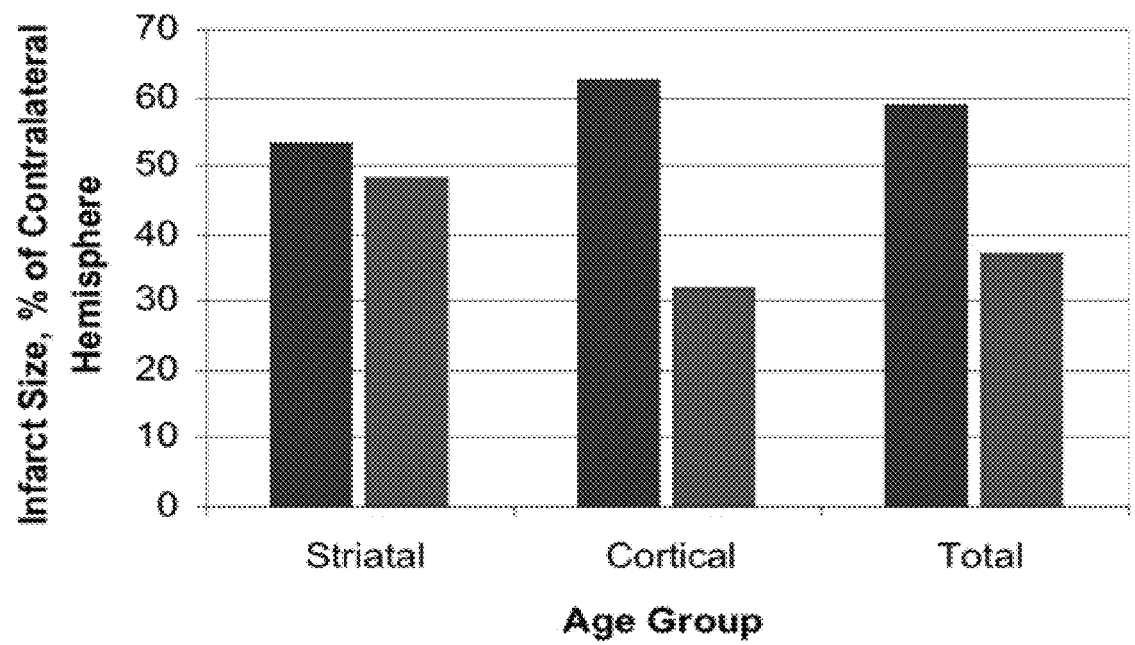
FIG. 1 shows reductions in cortical infarct area using TCP in a rat model of ischemic stroke.

The present invention is a neuroprotective mixture that protects against the devastating effects of strokes and aberrant cerebral perfusion states. In one of many possible embodiments, the neuroprotective mixture includes: 1) creatine, 2) a ketone body, and 3) a magnesium salt. In one of many possible embodiments of the invention, the creatine can be phosphocreatine (PCr), the ketone body can be β-hydroxybutyrate (BHB), and the magnesium salt can be magnesium gluconate (MgG). Optionally, but preferably, the PCr, BHB, and MgG are present in the mixture in a 2:1:2 molar ratio of PCr:MgG:BHB.

This neuroprotective mixture represents a novel approach to neuroprotection in several respects. First, the neuroprotective mixture is a combination of three separate chemical agents that favorably affect major adverse events involved in neuronal death. Together these three compounds create a tri-functional neuroprotective system that protects the brain, the blood vessels, and the blood brain barrier following stroke. These chemical agents have several mechanisms of action. This represents a significant departure from earlier neuroprotective trials that were one-dimensional in nature.

The neuroprotective mixture further provides a novel method of drug administration. The neuroprotective mixture can be administered as a daily oral supplement. By providing the neuroprotective mixture on a continuous daily basis, individuals receive neuronal protection in a preventative/prophylactic manner. Currently, there are no efficacious neuroprotective agents for acute ischemic/hemorrhagic stroke victims or patients that sustain aberrant cerebral perfusion states.

Magnesium.

Magnesium is a divalent metal cation. It is critical to numerous biological activities in the ionized and non-ionized (bound) forms. It is available in oral and intravenous (IV) formulations. It is utilized in medicine as the chloride, sulfate and citrate salts. Other forms include gluconate and other anions. There are multiple formulations of magnesium that have biological activity and bioavailability.

Recent evidence suggests that low levels of free magnesium (Mg++) in the blood may be correlated with poor neurological outcome in patients with strokes, head injury, and brain tumors. Mg++ has also been used as an anticonvulsant for pregnant women with pre-eclampsia and/or eclampsia, and may play a role in the treatment or prevention of cerebral vasospasm after subarachnoid hemorrhage.

Magnesium gluconate (MgG) is a potent calcium ion (CO channel blocker and $Ca^{++}$ antagonist. It can decrease $Ca^{++}$ overload in the cell and thus help decrease mitochondrial mediated apoptosis. MgG is safe and well-tolerated in humans and is a first line cerebral vascular protectant for pregnant women at risk for eclampsia.

MgG can be separated into magnesium ion and the gluconate ion. An alternative embodiment of the invention utilizes a compound of magnesium chloride and gluconic acid. A further alternative embodiment of the invention utilizes a compound of magnesium sulfate.

Magnesium sulfate has been successfully used in a number of animal models for neuron protection. It has been demonstrated in a fluid percussion model of head trauma that magnesium chloride limits the extent of neuronal injury in this model of diffuse neuronal injury. It also has been demonstrated that magnesium chloride has a similar effect in models of spinal cord ischemia. In a study utilizing magnesium therapy, imaging and spectroscopy, both magnesium sulfate and magnesium chloride were able to enter the cerebrospinal fluid (CSF) as well as alter the amount of neuronal injury and a diffuse anoxia injury model in rats.

Intraperitoneal injections of $MgCl_2$, at a dose of 1 mmol/kg given immediately after middle cerebral artery (MCA) occlusion in a rat model of ischemic infarct decreased the size of the measured infarct. $MgCl_2$ given via an intraperitoneal injection has been shown to reduce the average size of infarcts in a rat model of ischemia from 165 $mm^3$ to a 122 $mm^3$.

β-Hydroxybutyrate (BHB).

BHB is a reduced form of acetoacetate and the combination of BHB and acetoacetate are often referred to as ketone bodies. The ketone bodies are often and quickly interconverted in the body. BHB is an anion and is often found in salt forms. The salt forms of BHB include, but are not limited to, sodium salt, potassium salt, free acid, etc. These salts and the interconversion of the ketone bodies are extremely well established with documented biological activity and pharmacokinetics.

The human brain is dependent upon the presence of glucose for its metabolic needs, as the brain has essentially no glycogen reserves. The only exception to the brain's dependence upon glucose is that it can derive a major portion of its metabolic needs from the catabolism of ketone bodies such as BHB during periods when glucose is not available. BHB was first utilized as a cerebral protectant in an indirect manner. Since the early 1920's the use of a ketogenic diet has been known to influence the severity and frequency of seizures. The preliminary data supporting the beneficial effects of BHB as a cerebral protectant or neuroplegic solution following surgery: 1) the clinical efficacy of the ketogenic diet as an antiepileptic therapy, 2) the neuroprotective effects seen in vitro, and 3) the neuroprotective effects seen in the ketogenic state. These benefits are not likely to be mutually exclusive.

There are several hypotheses for the antiepileptic effects of ketones. One is that the ketones may have an energetic benefit (as discussed previously); the second is that the ketones, specifically BHB, may decrease neural excitability; and the third is that the extracellular fluid composition is changed with increased ketones and that this impacts on epileptic discharges. As has been suggested previously, ketones may benefit the brain, neural and vascular tissue by providing an energetic benefit.

BHB is a naturally occurring ketone body that normally circulates in the blood stream at levels of 0.1 to 10 mM. BHB is readily utilized by the brain as an energy source when glucose is limited. Inside the cell, BHB normalizes mitochondrial function and decreases mitochondrial derived reactive oxygen species. Its putative antiepileptogenic activity is also important, as seizures following surgery are a relatively common complication. BHB may prevent seizures by antagonizing some of the excitotoxic effects of glutamate.

An alternative embodiment of the invention utilizes acetoacetate in combination with, or instead of, BHB. Acetoacetate is synthesized in the liver from acetyl-CoA. Acetoacetate is a true ketone and is reduced to BHB in a typical redox reaction using NADH as the reducing equivalent. This investment in reducing power has two important beneficial effects for the BHB in its role as a neuroprotective. The first is that BHB is more stable than acetoacetate and is less likely to cause acidosis. Ketoacidosis occurs in diabetic patients from the production of acetone via a spontaneous, irreversible and non-enzymatic decarboxylation of acetoacetate. The production of acetone and the acidosis associated with the liberated $CO_2$ makes acetoacetate a poor choice for a ketone based neural protectant. BHB, however, is more thermodynamically stable and is able to produce NADH in the brain when it is oxidized to acetoacetate. Therefore, BHB is able to quickly provide energy for the brain, without the risk of ketoacidosis.

Phosphocreatine (PCr).

Phosphocreatine contains one phosphate and one creatine molecule and typically is marketed as a sodium salt. It stabilizes membranes and protects against apoptosis by influencing the mitochondrial creatine kinase. It also plays a critical role in energy management and protection against free oxygen radicals. Clearance from the blood stream has a fast and slow half-life, and it can be broken down to creatine and phosphate. Creatine and phosphate both enter cells and can be reconverted to phosphocreatine in the cell and therefore can be beneficial to the cells following stroke. The neuroprotective mixture optionally but preferably contains about 4 mM of phosphocreatine.

Phosphocreatine is the phosphorylated version of creatine and as a high energy phosphate phosphocreatine can be used to buffer the ATP concentration. Phosphocreatine is ionic and can be purchased and administered as a sodium salt, potassium salt, acid and similar salt formulations. Creatine is readily converted into phosphocreatine in numerous cells included brain cells. Creatine comes in numerous formulations that have been established to be biologically active. In summary phosphocreatine and creatine formulations are numerous and characterized.

EXAMPLES

Ischemic Stroke Model Studies

As shown in FIG. 1, the mixture of the present invention (TCP) has been shown to be protective against ischemic damage in the cortical region. Control animals demonstrated cerebral cortical infarctions comprising a mean infarct area of 62.5±8.5%, while animals receiving the TCP neuroprotectant at ninety (90) minutes post-occlusion showed a reduction in infarct area to 30±3.5%.

Figure 2:
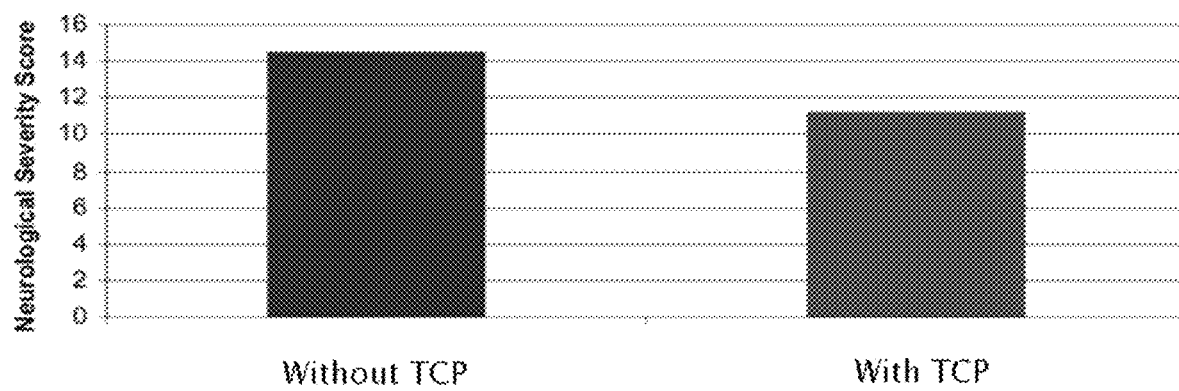
FIG. 2 shows improvement in functional outcomes with TCP in a rat model of ischemic stroke.

As shown in FIG. 2, functional outcomes based on a modified neurologic severity scale were statistically improved in animals treated with TCP.

Figure 3:
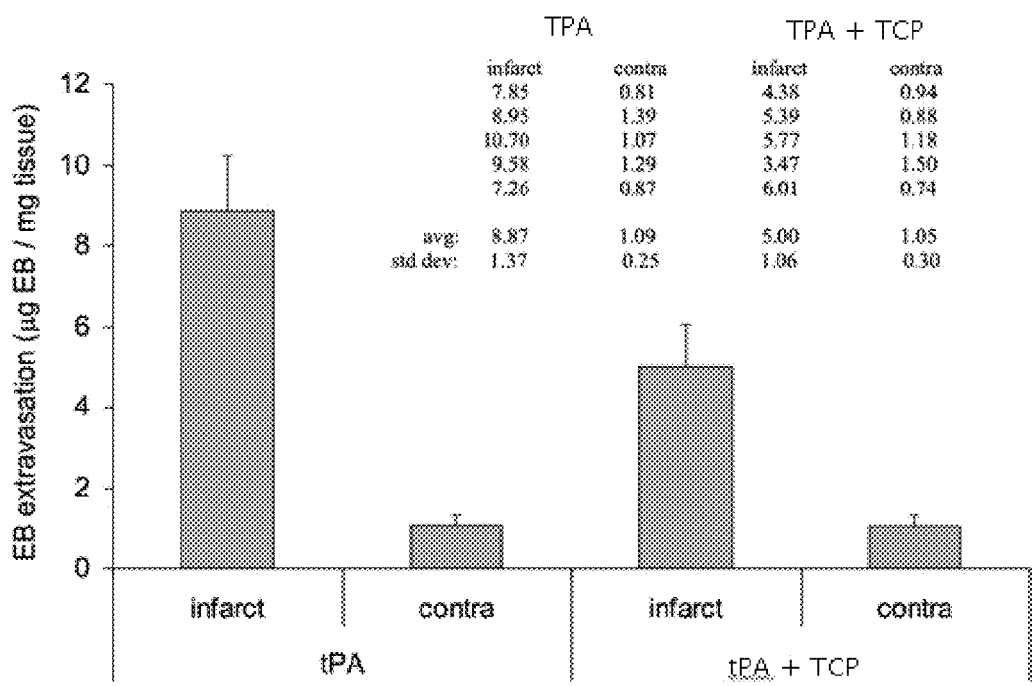
FIG. 3 shows improved blood brain barrier integrity with TCP administration in a rat model of ischemic stroke.

Evidence also demonstrates that TCP can reduce disruption to the blood brain barrier following an ischemic insult. Blood brain barrier extravasation studies utilizing Evan's Blue dye demonstrated a significant decrease in extravasation within groups receiving the invention alone as well as a synergistic effect in animals receiving both the invention and tPA (FIG. 3).

Additional studies using a validated rat model for ischemic stroke have also been conducted. These studies made comparisons in stroke volumes between five different treatment groups:

a. Ischemic stroke model in aged rats; no reperfusion; no neuroprotection b. Ischemic stroke model in aged rats; no reperfusion; neuroprotection administered c. Ischemic stroke model in aged rats; reperfusion (tPA) given; no neuroprotection d. Ischemic model in young rats; no reperfusion; no neuroprotection e. Ischemic stroke model in young rats; reperfusion (tPA) given; no neuroprotection Table 1 provides data on the infarct volumes in these five separate treatment groups. As reflected in the table, neuroprotection with TCP alone not only demonstrated reductions in infarct volume, but it also shows a favorable synergistic effect when combined with the thrombolytic agent, tPA.

TABLE 1

Infarct volumes by treatment groups in a rat model of ischemic stroke.

| | Aged | | Aged + TCP | | Aged + tPA | |
|---|---|---|---|---|---|---|
| | Infarct | Contra | Infarct | Contra | Infarct | Contra |
| | 10.86 | 1.18 | 11.27 | 1.15 | 7.85 | 0.81 |
| | 16.99 | 1.62 | 8.2 | 1.23 | 8.95 | 1.39 |
| | 11.3 | 1.52 | 8.43 | 1.43 | 10.7 | 1.07 |
| | 11.27 | 0.66 | 9.31 | 0.59 | 9.58 | 1.29 |
| | 14.17 | 2.08 | 10.52 | 1.36 | 7.26 | 0.87 |
| Average | 12.918 | 1.412 | 9.546 | 1.152 | 8.868 | 1.086 |
| Std Dev | 2.63 | 0.53 | 1.33 | 0.33 | 1.37 | 0.25 |
| Std Err | 1.175173504 | 0.23627841 | 0.591990209 | 0.14848029 | 0.610966492 | 0.113185271 |

TABLE 1-continued

Infarct volumes by treatment groups in a rat model of ischemic stroke.

| | Aged + TCP + tPA | | Young | | Young + tPA | |
|---|---|---|---|---|---|---|
| | Infarct | Contra | Infarct | Contra | Infarct | Contra |
| | 4.38 | 0.94 | 7.06 | 0.84 | 3.75 | 1.07 |
| | 5.39 | 0.88 | 8.69 | 1.03 | 4.35 | 1.28 |
| | 5.77 | 1.18 | 8.29 | 1.02 | 3.64 | 1.66 |
| | 3.47 | 1.5 | 7.85 | 0.89 | 4.1 | 0.52 |
| | 6.01 | 0.74 | 8.17 | 1.36 | 5.2 | 1.36 |
| Average | 5.004 | 1.048 | 8.012 | 1.028 | 4.208 | 1.178 |
| Std Dev | 1.06 | 0.30 | 0.61 | 0.20 | 0.62 | 0.42 |
| Std Err | 0.472999446 | 0.133272201 | 0.272877068 | 0.090582106 | 0.277745312 | 0.189466726 |

| | Aged | Aged + TCP | Aged + tPA | Aged + tPA + TCP | Young | Young + tPA |
|---|---|---|---|---|---|---|
| Ipsilateral | 12.9 | 9.5 | 8.9 | 5 | 8 | 4.2 |
| Contralateral | 1.4 | 1.2 | 1.1 | 1.1 | 1 | 1.2 |

Figure 4:
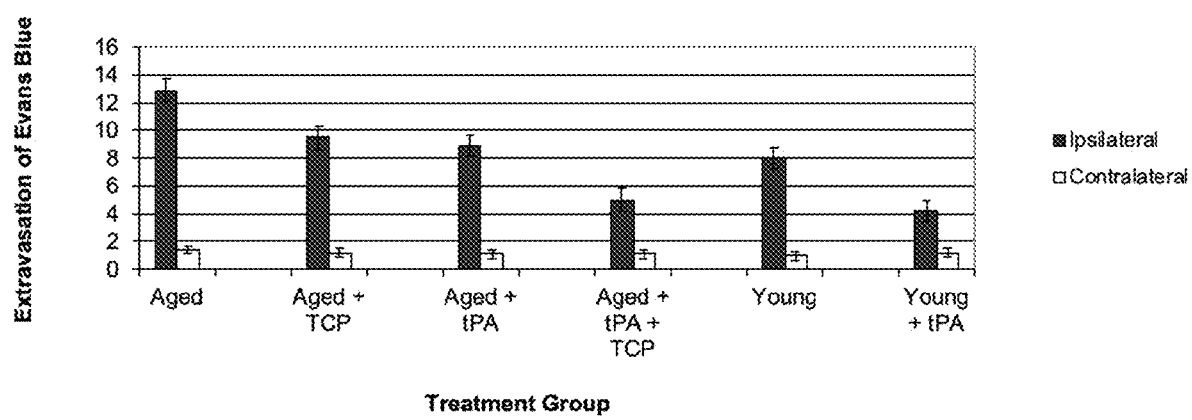
FIG. 4 shows extravasation of Evans Blue in 5 separate treatment groups using an ischemic stroke model in rats.

These same animal cohorts were evaluated for blood brain barrier integrity by staining with Evans Blue dye. FIG. 4 shows the favorable impact of the invention alone on blood brain barrier integrity as well as its combined administration with tPA. This data provides evidence of a favorable synergistic effect when the invention is combined with thrombolytic therapy.

Hemorrhagic Stroke Model Studies

Further studies in a hemorrhagic stroke model were performed using the neuroprotective mixture containing phosphocreatine, beta-hydroxybutyrate, and magnesium gluconate. A buffered solution of 50:25:50 mM PCr:MgG:BHB was prepared. This solution, which is buffered with NaOH and iso-osmotic with NaCl, is sufficient for increasing MgG to a target dose, which preferably is not to exceed 2 mM. The mixture was dissolved and buffered to a neutral pH, freeze dried for storage, and resuspended for IV use. The solution was administered intraperitoneally (IP) in rats.

Figure 5:
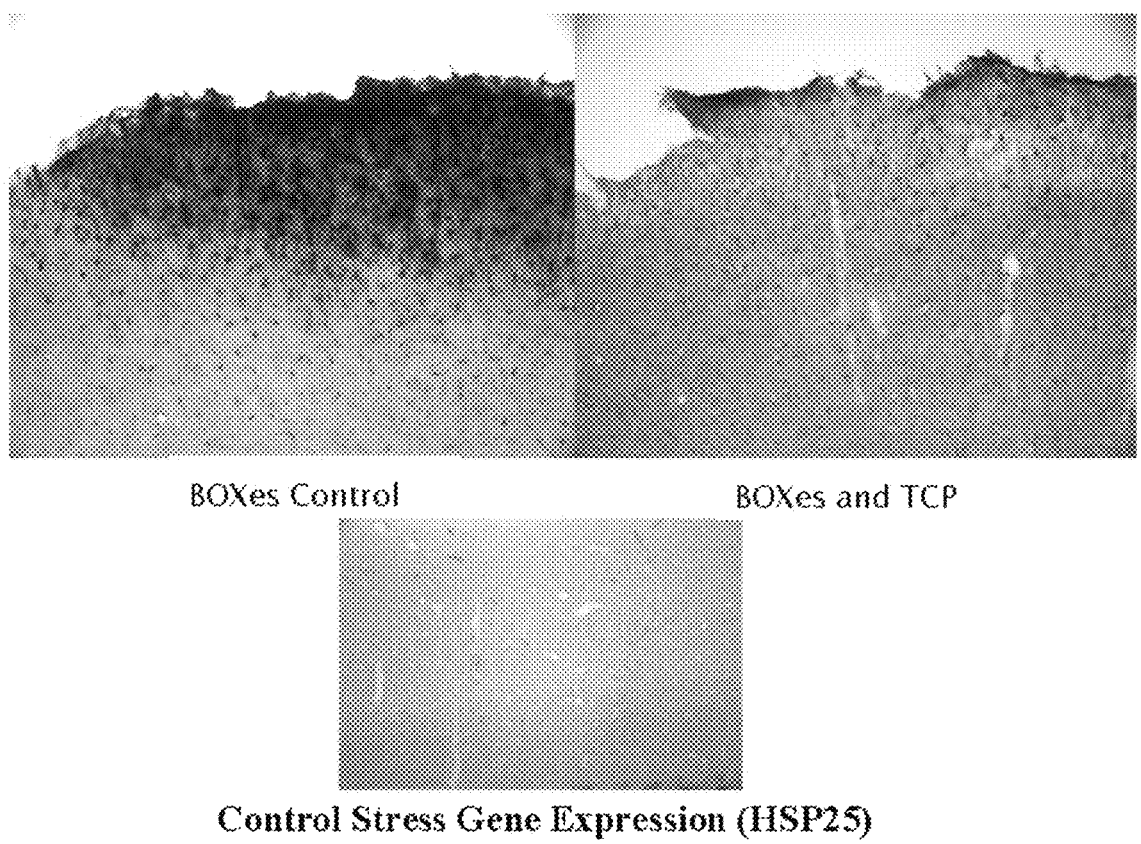
FIG. 5 shows reduced expression of HSP25 using TCP in a hemorrhagic stroke model in rats.

As shown in FIG. 5, the IP administration of the neuroprotective mixture was neuroprotective following a model of hemorrhagic stroke. The neuroprotection was assessed by a decrease in stress gene expression. Specifically, heat shock protein 25 (HSP25) was measured since it is a well-documented marker of neuronal stress. BOXes stands for bilirubin oxidation products. There are two BOXes; BOX-A and BOX-B. These two BOXes are isomers derived from the two ends of the bilirubin molecule. BOXes are thought to be produced post brain hemorrhage, such as subarachnoid hemorrhage. When produced, they have neurologic toxic and vasoactive activity in the tissue surrounding the hemorrhage. As an established toxic metabolite produced post brain hemorrhage, BOXes are often used as a mechanism of pathology post hemorrhaging in the brain.

Figure 6:
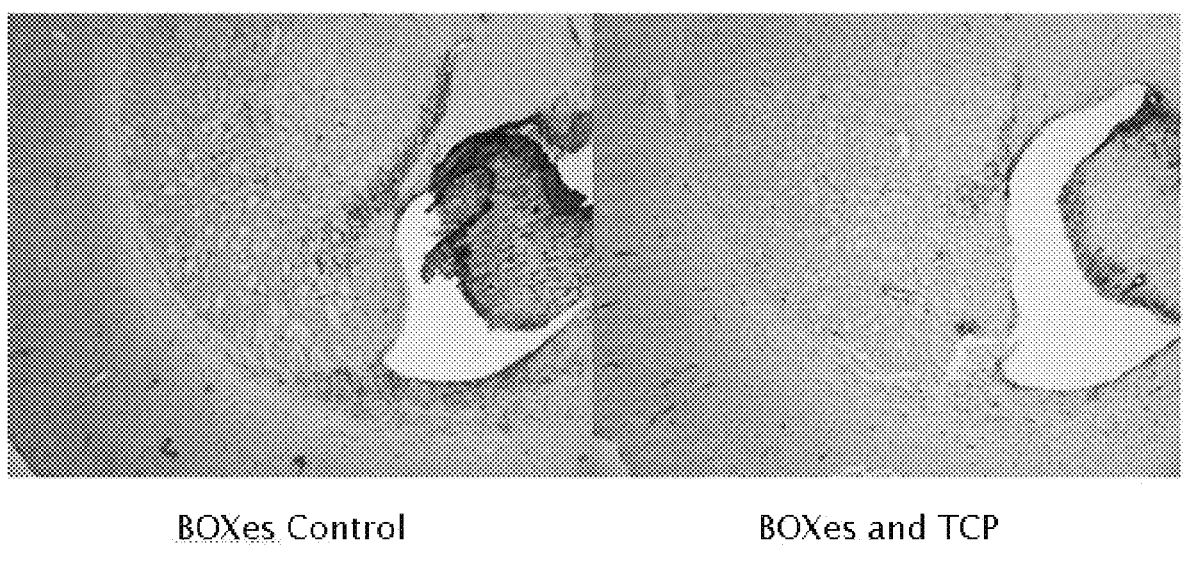
FIG. 6 shows reduced expression of HSP25 using TCP in a hemorrhagic stroke model.

Using a hemorrhagic stroke model, IP injections of TPC during the stroke lead to significant neuroprotection. The protection observed in these figures is largely in the glial cells via decreased heat shock protein expression (FIG. 6). This has been studied in rats with the TCP neuroprotective mixture and rats without the mixture. The neuroprotective benefits of the TCP mixture are shown consistently in the animals studied to date. Safety studies also were performed on rats, and the TCP neuroprotective mixture caused no detectible detrimental effects.

The data demonstrate that the TCP neuroprotective mixture benefits vascular and neural tissues intracellularly and extracellularly against various models of ischemic and hemorrhagic stroke. These data also demonstrate that the TCP neuroprotective mixture can protect the brains in vivo from stress as assessed by stress gene expression (HSP25). Moreover, the target doses for the TCP neuroprotective mixture have no detectible detrimental effects in the rats.

Prophylactic Neuroprotection in the Ischemic Model

Additional studies have been conducted where the TCP neuroprotective mixture was administered prior to the neurologic insult in the animal model. A buffered solution of 50:25:50 mM PCr:MgG:BHB was prepared. This solution, which is buffered with NaOH and iso-osmotic with NaCl, is sufficient for increasing MgG to our target dose which is not to exceed 2 mM. We have demonstrated previously that this solution is buffered and does not significantly change human blood pH using a target dose in vitro of 6 mM.

Ten (10) minutes of hemispheric ischemia was preceded by IP administration of the TCP neuroprotective mixture in gerbils. The TCP neuroprotective mixture was administered at the same dose as for the hemorrhagic rat experiments in a 2:1:2 ratio of phosphocreatine:magnesium gluconate:beta-hydroxybutyrate. Three animals received the TCP neuroprotective mixture and three control animals received saline injections. One of the control animals died within 10 minutes of the procedure, whereas none of the animals that received the TCP neuroprotective mixture died.

Figure 7:
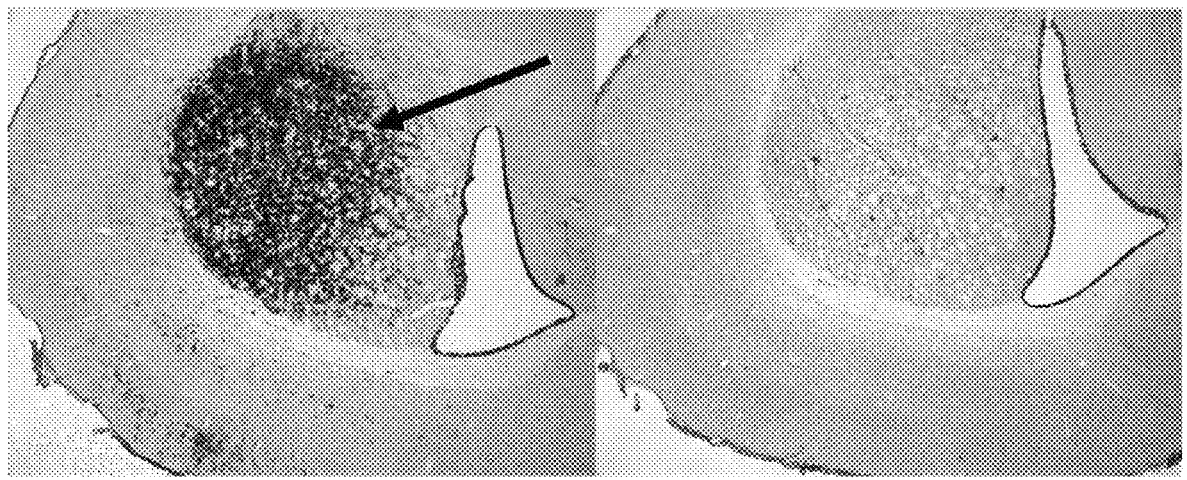
FIG. 7 shows reductions in HSP25 expression using TCP pre-treatment in an ischemic stroke model in gerbils.
Figure 8:
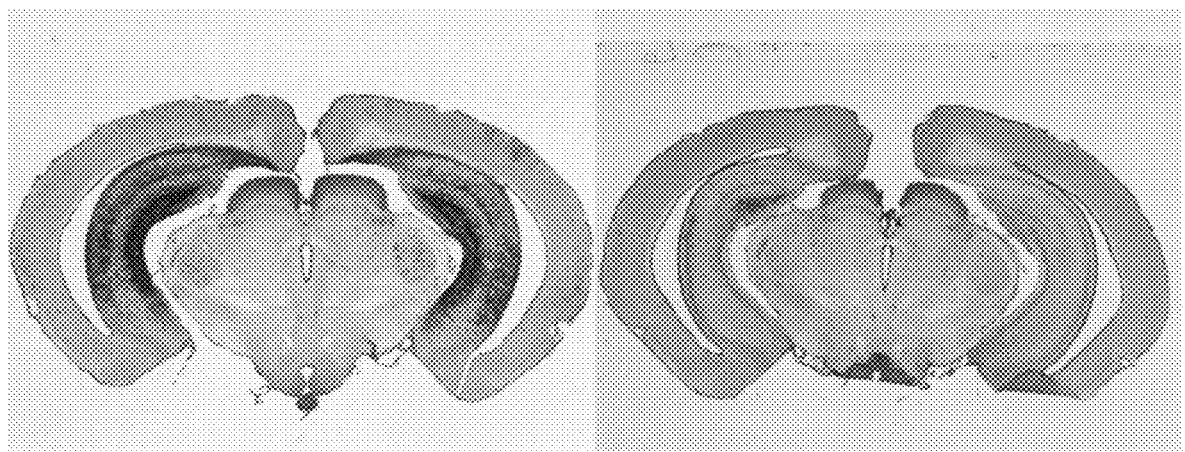
FIG. 8 shows reductions in HSP25 expression with TCP pre-treatment in an ischemic stroke model in gerbils.

During recovery, the TCP neuroprotective mixture animals appeared to begin walking, grooming and investigating their surroundings faster than the saline control animals. Twenty-four (24) hours after the ischemic insult, all of the TCP neuroprotective mixture animals were alive and behaving normally. The two surviving control animals appeared normal as well. At 24 hours post ischemia, the gerbils were anesthetized and the brains perfusion fixed. Upon histological examination we assessed stress gene expression (HSP-25, HO-1, and HSP-70) in the brains. There was greater stress gene expression in the ischemic hemisphere of the saline control animals as compared to the non-ischemic hemisphere. FIGS. 7 and 8 show the expression of HSP-25 in the ischemic hemisphere of a representative saline control and neuroprotective mixture brain. There is greater expression of HSP25 in the saline control animal as indicated with the dark staining (arrow) compared to the neuroprotective mixture animal. This was a consistent result with all of the surviving animals. Thus, the TCP neuroprotective mixture can protect the brain from ischemic events.

Figure 9:
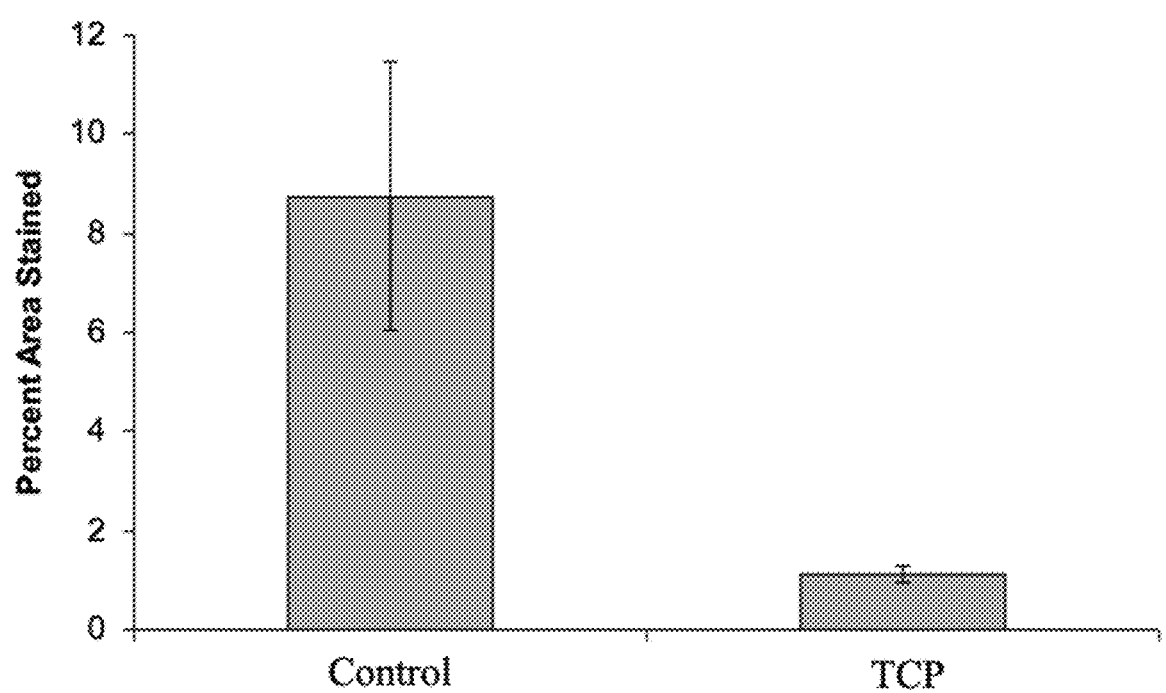
FIG. 9 shows reductions in HSP25 expression when pre-treatment with TCP is provided in an ischemic stroke model in gerbils.

Furthermore, as shown in FIG. 9, we have quantified the reductions in stress gene expression when pre-treatment with the TCP neuroprotective mixture is administered in the ischemic stroke model in gerbils.

CONCLUSION

While various embodiments of the present invention have been described above, it should be understood that they have been presented by way of example only, and not limitation. It will be understood by those skilled in the art that various changes in form and details may be made therein without departing from the spirit and scope of the invention. Thus, the breadth and scope of the invention should not be limited by any of the above-described exemplary embodiments.

What is claimed is:

1. A method of mitigating the harmful effects of ischemic stroke in a person, comprising administering to that person a dietary supplement comprising a mixture of phosphocreatine, magnesium gluconate, and beta hydroxybutyrate in a 2:1:2 ratio, wherein the supplement is administered orally on a daily basis prior to the occurrence of a stroke to mitigate the harmful effects on the person of having a stroke.

* * * * *